United States Patent
Narumi et al.

(10) Patent No.: US 7,691,975 B2
(45) Date of Patent: Apr. 6, 2010

(54) INTERFERON-β COMPLEX

(75) Inventors: Hideki Narumi, Kamakura (JP); Yoshiaki Tsushima, Kamakura (JP); Koji Yamashita, Fujisawa (JP); Saburou Sone, Yokohama (JP); Miyuki Sato, Kamakura (JP)

(73) Assignees: Toray Industries, Inc. (JP); Tadatsugu Taniguchi (JP)

( * ) Notice: Subject to any disclaimer, the term of this patent is extended or adjusted under 35 U.S.C. 154(b) by 610 days.

(21) Appl. No.: 10/569,211

(22) PCT Filed: Aug. 24, 2004

(86) PCT No.: PCT/JP2004/012452

§ 371 (c)(1),
(2), (4) Date: Feb. 24, 2006

(87) PCT Pub. No.: WO2005/019260

PCT Pub. Date: Mar. 3, 2005

(65) Prior Publication Data

US 2006/0246034 A1  Nov. 2, 2006

(30) Foreign Application Priority Data

Aug. 25, 2003  (JP) .............................. 2003-299850

(51) Int. Cl.
- *C07K 14/00* (2006.01)
- *A61K 38/21* (2006.01)
- *A61K 38/00* (2006.01)

(52) U.S. Cl. ........................... 530/351; 424/85.6; 514/2

(58) Field of Classification Search ........................ None
See application file for complete search history.

(56) References Cited

U.S. PATENT DOCUMENTS

| | | | |
|---|---|---|---|
| 4,766,106 A | 8/1988 | Katre et al. | |
| 4,917,888 A | 4/1990 | Katre et al. | |
| 2003/0219404 A1 | 11/2003 | Yamasaki et al. | |
| 2004/0115168 A1 * | 6/2004 | DeFrees et al. | 424/85.6 |

FOREIGN PATENT DOCUMENTS

| | | |
|---|---|---|
| JP | 60-226821 A | 11/1985 |
| JP | 9-25298 A | 1/1997 |
| JP | 2004-35515 A | 2/2004 |
| WO | WO 87-00056 A1 | 1/1987 |
| WO | WO 96/11953 A1 | 4/1996 |
| WO | WO 00/23114 A2 | 4/2000 |
| WO | WO 01/15736 A2 | 3/2001 |
| WO | WO 01/48052 A1 | 7/2001 |

OTHER PUBLICATIONS

Seth P. Monkarsh et al., *Isolation of Positional Isomers of Mono-poly(ethylene glycol)ylated Interferon/α-2a and the Determination of Their Biochemical and Biological Characteristics*, ACS Symposium Series 680, © 1997 American Chemical Society, pp. 207-216.

R. Blake Pepinsky et al., *Improved Pharmacokinetic Properties of a Polyethylene Glycol-Modified Form of Interferon-β-1a with Preserved in Vitro Bioactivity*, The Journal of Pharmacology and Experimental Therapeutics, © 2001 by The American Society for Pharmacology and Experimental Therapeutics, Jun. 2001, vol. 297, No. 3, pp. 1059-1066.

Stefan Foser et al., *Isolation, Structural Characterization, and Antiviral Activity of Positional Isomers of Monopegylated Interferon α-2a (PEGASYS)*, Protein Expression & Purification, © 2003 Elsevier Science (USA), Jul. 2003, vol. 30, No. 1, pp. 78-87.

* cited by examiner

*Primary Examiner*—Gary B Nickol
*Assistant Examiner*—Bruce D Hissong
(74) *Attorney, Agent, or Firm*—DLA Piper LLP (US)

(57) ABSTRACT

The present invention relates to a complex between interferon-β and polyethylene glycol, which has high biological activity, and to a method for producing the complex at high efficiency. Namely, the present invention relates to a method for producing an interferon-β complex comprising binding interferon-β to polyethylene glycol in the presence of at least one additive selected from the group consisting of oligosaccharides having 5 or less sugar units, monosaccharides, their corresponding sugar alcohols, and $C_{2-6}$ polyhydric alcohols, and to an interferon-β complex produced by the method, which has polyethylene glycol specifically bound with lysine located at the 19th or 134th position in the amino acid sequence of interferon-β.

9 Claims, 10 Drawing Sheets

Fig. 4

```
    K1                        ↓ K2
n-MSYNLLGFLQ  RSSNFQCQKL  LWQLNGRLEY   30
  ↓ K3          ↓ K4       ↓ K5
  CLKDRMNFDI  PEEIQKLQQF  QKEDAALTIY   60

EMLQNIFAIF  RQDSSSTGWN  ETNIVELLAN   90
         ↓K6   K7↓  ↓K8           ↓ K9
  VYHQINHLKT  VLEEKLEKED  FTRGKLMSSL  120
    ↓ K10      K11↓ ↓K12
  HLKRYYGRIL  HYLKAKEYSH  CAWTIVRVEI  150

LRNFYFINRL  TGYLRN
```

INTERFERON-β COMPLEX

TECHNICAL FIELD

The present invention relates to an interferon-β complex having polyethylene glycol specifically bound to lysine located at the 19th or 134th position in the amino acid sequence of interferon-β, and to a production method thereof.

BACKGROUND ART

Water-soluble polymers such as polyethylene glycol, when bound to biomolecules as typified by protein drugs, are known to confer clinical usefulness in ways that bring about effects such as improved physical and thermal stability, resistance to protease, and solubility as well as decreased in vivo distribution volume and improved retention in blood (see Inada et al., J. Bioact and Compatible Polymers 5,343(1990); Delgado et al., Critical Reviews in Therapeutic Drug Carrier Systems 9,249 (1992); and Katre, Advanced Drug Delivery Reviews 10,91(1993)).

A variety of methods are available for binding natural interferon-β or interferon-β having a primary structure identical to natural one to a water-soluble polymer polyethylene glycol (PEG). For example, Katre et al have applied the amino group modification of lysine or the like to the PEGylation of interferon-β (see U.S. Pat. Nos. 4,766,106 and 4,917,888 and International Publication No. WO87/00056). Specifically, they have reported a conjugate obtained by binding a water-soluble polymer (PEG) having a molecular weight of 300 to 100,000 to recombinant interferon-β or IL-2 via 1 to 10 lysine residues in the amino acid sequence thereof. Alternatively, a technique for binding PEG to an amino group in lymphokine has already been reported in "Chemically modified lymphokine and production thereof" (see JP Patent Publication (Kokai) No. 60-226821A (1985)). However, in reality, interferon-β bound with PEG by these methods has interferon-β activity decreased to less than 10% and can not be in practical use.

No previous report has described a technique for selectively binding PEG to the amino group of particular lysine in interferon-β. If it is possible to select and specifically modify lysine that minimizes the rate of reduction in interferon-β biological activity caused by PEG binding, reduction in the total amount of proteins administered as a pharmaceutical drug leads to fewer side effects to patients and further to easier quality control.

On the other hand, a method is also known which uses reductive alkylation without involving lysine residues to selectively bind a water-soluble polymer to the amino terminus of interferon through reaction at pH suitable for the selective activation of the amino-terminal α-amino group of the interferon (see JP Patent Publication (Kokai) No. 9-25298A (1997)). However, in reality, the PEGylation of interferon-β by this method does not give mono-PEGylation and brings about nonselective PEGylation at any lysine residue or the N terminus, resulting in the generation of a heterogeneous mixture without sufficient antiviral activity and cell growth-inhibiting activity.

More importantly, purified interferon-β N-terminally bound with PEG is also known to have remaining activity (ratio with respect to interferon-β activity before binding) dramatically decreased when the PEG has a molecular weight higher than 20,000 and to completely lack activity when the PEG has a molecular weight of 40,000, as reported by Pepinsky et al (see Pepinsky et al., The Journal of Pharmacology and Experimental Therapeutics, vol. 297, p 1059-1066, (2001)).

As for interferon-α, Bailon et al have produced interferon-α nonselectively mono-PEGylated at the lysine residue with a branched polymer PEG having a molecular weight of 40,000 (Bailon et al., Bioconjugate Chem. 12, 195 (2001)). However, they have reported that the remaining activity of interferon-α bound with PEG having a molecular weight as high as 40,000 is significantly decreased, as in the case with interferon-β N-terminally bound with PEG, and is 7%.

Namely, it is difficult to directly apply techniques (the number and position of PEG bound) that have been developed for modification with low molecular weight PEG to high molecular weight PEG. Thus, a novel technique has been required for producing a highly active interferon-β complex bound with PEG having a molecular weight (20,000 or higher) necessary to sufficiently obtain effects such as extended in vivo circulatory half-life and decreased clearance values that lead to usefulness as a pharmaceutical drug.

As described above, there has been no report so far on the selection of a lysine residue to be modified for avoiding reduction in the activity of interferon-β bound with a high molecular weight water-soluble polymer, and on a technique for this purpose. Moreover, there has been no report that the selective binding of a high molecular weight water-soluble polymer such as PEG to any one of 11 lysine residues present in interferon-β produces a highly active interferon-β complex.

DISCLOSURE OF THE INVENTION

An object of the present invention is to find a structure of an interferon-β complex that has no impairment of biological activity even by the modification with a high molecular weight substance such as polyethylene glycol and to provide a method for producing such complex at high efficiency. Particularly, an object of the present invention is to obtain an interferon-β complex in which 10% or higher of interferon-β activity is maintained even by the binding of PEG having a molecular weight as high as 40,000.

The present inventors have conducted a variety of studies for attaining the objects and have consequently found that natural interferon-β has sugar chain-linked asparagine at the 80th position, and means for minimizing reduction in its activity is the selective modification of a lysine residue located at 19th or 134th position, which is proximal to this asparagine from the viewpoint of the three-dimensional structure, with a high molecular weight substance. Even when a polymer (e.g., PEG) having a molecular weight that exceeds 10,000 is used, the selective binding of the polymer to the lysine located at the 19th or 134th position can minimize reduction in interferon-β activity.

The lysine residue located at the 19th position has previously been listed as one of lysine residues that should be removed when PEG is bound to the amino group of interferon-β (see International Publication No. WO01/15736). WO01/15736 teaches that commercial preparations of interferon-β are sold under the name BETASERON® (also termed interferon β1b, which is non-glycosylated, produced using recombinant bacterial cells, has a deletion of the N-terminal methionine residue and the C17S mutation). Therefore, this binding site cannot be expected from conventional techniques. As for the lysine residue located at the 134th position as well, there has been no report so far that the selective binding of a high molecular weight modifying substance to this site minimizes reduction in interferon-β activity.

Namely, the present invention provides a method for producing an interferon-β complex comprising binding interferon-β to polyethylene glycol in the presence of at least one additive selected from the group consisting of oligosaccharides having 5 or less sugar units, monosaccharides, their corresponding sugar alcohols, and $C_{2-6}$ polyhydric alcohols. The present invention also provides an interferon-β complex produced by the method, particularly an interferon-β complex characterized in that the complex is produced by specifically binding polyethylene glycol to lysine located at the 19th or 134th position in the amino acid sequence of interferon-β.

The interferon-β complex of the present invention has high blood solubility, interferon-β activity, and physical and biological stability and is useful as a pharmaceutical drug in the treatment, prevention, and alleviation of all symptoms and diseases to which interferon-β is applied.

BRIEF DESCRIPTION OF THE DRAWINGS

FIG. 4 is a diagram showing the amino acid sequence of interferon-β SEQ ID NO: 1 and predicted lysyl endopeptidase cleavage sites therein;

Figure 1:
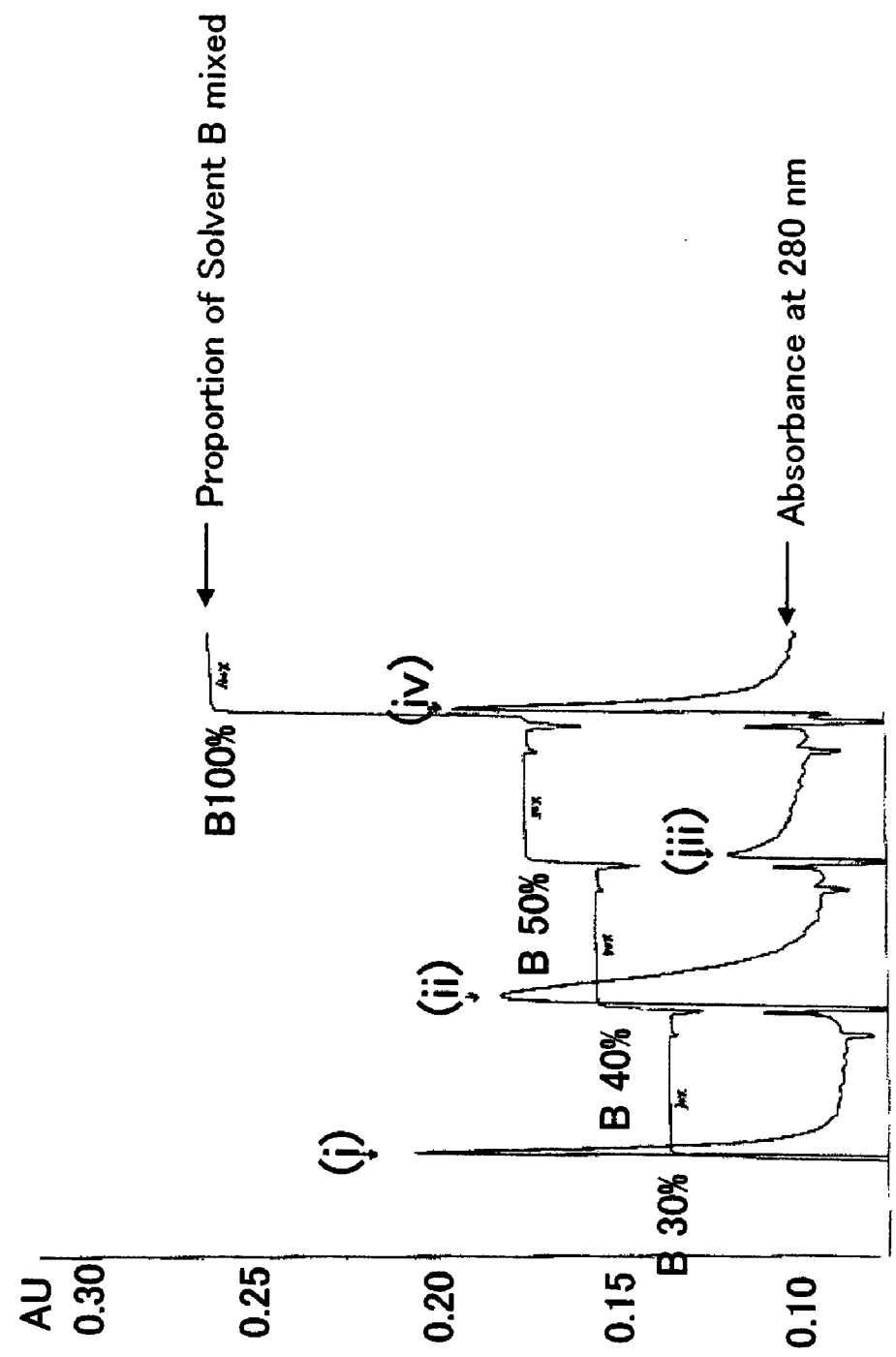
FIG. 1 is a diagram showing the Poros HS column separation and purification of an interferon-β complex having polyethylene glycol bound with the amino group of lysine located at the 19th position. In the drawing, the upper arrow denotes the proportion of Solvent B mixed, and the lower arrow denotes absorbance at 280 nm.

The present specification encompasses contents described in the specification of Japanese Patent Application No. 2003-299850 that serves as a basis for the priority of the present application.

BEST MODE FOR CARRYING OUT THE INVENTION

As described above, a method of the present invention can efficiently bind polyethylene glycol to lysine located at the 19th or 134th position in the amino acid sequence of interferon-β and separate unbound products and by-products therefrom.

Natural interferon-β, interferon-β having a sugar chain altered from natural one, or recombinant interferon-β with or without a sugar chain can be used as the interferon-β subjected to the method of the present invention. In the method of the present invention, a commercially available product may be used as such interferon-β. Natural interferon-β has sugar chain-linked asparagine at the 80th position that is proximal to lysine located at 19th position from the viewpoint of the three-dimensional structure. When high molecular weight PEG or the like is bound thereto, it is preferred to use recombinant interferon-β without a sugar chain because possible steric hindrance reduces reaction efficiency. Any of those having the amino acid sequence of natural interferon-β with the deletion, substitution, or addition of one or several amino acids can also be used as the interferon-β subjected to the method of the present invention.

The interferon-β of the present invention also encompasses natural interferon-β, recombinant interferon-β, and an altered form thereof. The altered form means any of those obtained by altering or modifying the amino acid sequence or sugar chain of natural interferon as described above. In the present specification, the lysine located at the 19th or 134th position is represented by the amino acid number for the amino acid sequence of this natural interferon-β (FIG. 4 and SEQ ID NO: 1). The amino acid number of such lysine for the altered form is changed in ways that correspond to the position of the lysine in the amino acid sequence of the natural interferon-β.

The interferon-β in any of these forms may be obtained by any method such as extraction from tissue, protein synthesis, and biological production using natural or recombinant cells. Genetically engineered interferon-β without a sugar chain is commercially available, and such commercially available interferon-β can also be used in the method of the present invention.

Polyethylene glycol (PEG) is harmless to human bodies and, when administered as an interferon-β complex bound therewith, confers water solubility at a level necessary to dissolve the complex in blood. It is known in the art that the binding of PEG to a physiologically active substance allows the physiologically active substance in living bodies to attain improved physical and thermal stability, protection against enzymatic degradation, enhanced solubility, extended in vivo circulatory half-life, and decreased clearance values. In light of such effects, PEG can preferably be used in the present invention.

Any method may be used in PEG terminal activation for binding PEG to the amino group of the lysine residue in interferon-β. For example, PEG having an amino-reactive structure such as a hydroxysuccinimide ester or nitrobenzene sulfonate ester structure at the terminus can be employed. In the present specification, any of these terminal structures is referred to as an "amino-reactive functional group," and PEG having any of these terminal structures is referred to as "polyethylene glycol activated with an amino-reactive functional group." The PEG having any of these structures is conventionally in wide use for the binding with an amino group and can be produced with ease by a synthetic method commonly known or is commercially available. In the present invention, such a commercially available product can also preferably be used.

The average molecular weight of the PEG is not particularly limited and however, is preferably approximately 10,000 to 60,000, more preferably approximately 20,000 to 40,000, from the viewpoint of allowing interferon-β in living bodies to attain physical and thermal stability, protection against enzymatic degradation, enhanced solubility, extended in vivo circulatory half-life, and decreased clearance values.

The binding reaction between interferon-β and PEG can be performed by reacting interferon-β with PEG at pH 5.0 to 8.5, preferably pH 5.5 to 8.0, and in the presence of an anti-reduction agent for interferon-β activity, preferably in a buffer solution such as phosphate or citrate buffer solutions. The anti-reduction agent for interferon-β activity not only suppresses the aggregation of interferon-β caused by its being placed under the atmosphere of pH 5.0 to 8.5 suitable for the reaction, but also helps the specific binding reaction of PEG to the targeted lysine located at the 19th or 134th position or a site proximal thereto. Examples of the anti-reduction agent for interferon-β activity for efficiently binding PEG to the desired site with interferon-β activity maintained can include saccharides, among others, oligosaccharides having 5 or less sugar units, monosaccharides, their corresponding sugar alcohols, $C_{2-6}$ polyhydric alcohols. Particularly preferred are disaccharides or monosaccharides such as glucose, mannitol, sorbitol, sucrose, or trehalose, their corresponding sugar alcohols, and $C_{2-3}$ polyhydric alcohols such as ethylene glycol or glycerol. These anti-reduction agents for interferon-β activity can be used alone or in any combination of two or more of them.

The concentration of the anti-reduction agent for interferon-β activity subjected to the method of the present invention is not particularly limited and however, is approximately 1 to 90% (in total, when plural anti-reduction agents for interferon-β activity are used; hereinafter, specified in the same way), more preferably approximately 1 to 50%, even more preferably approximately 10 to 30%, with respect to the total weight of the reaction mixture. An interferon-β: PEG mixture ratio is not particularly limited and however, is typically approximately 1:1 to 1:400 molar ratio and preferably approximately 1:4 to 1:100 molar ratio for PEG activated with succinimidyl ester. A reaction temperature suitable for the method of the present invention is typically 4 to 40° C., preferably 4 to 25° C. Although a reaction time is appropriately determined according to the reaction temperature and so on, approximately 1 hour to 24 hours are typically adequate.

Polyethylene glycol can be bound specifically to lysine located at the 19th or 134th position in the amino acid sequence of interferon-β or to a site sterically proximal thereto by the reaction process. The "site sterically proximal thereto" refers to a nearby site in the active conformation of interferon-β and concretely, is cysteine located at the 17th position or asparagine located at the 80th position (particularly, a sugar chain linked thereto) for the lysine located at the 19th position. Moreover, the term "specific" or "specifically" refers to the selective and preferential binding of polyethylene glycol to the lysine located at the 19th or 134th position or to the site sterically proximal thereto. This specific binding gives homogeneous mono-PEGylated interferon-β.

A water-soluble polymer having a thiol-reactive structure such as an orthopyridyl disulfide, vinyl sulfone, maleimide, or iodoacetamide structure at the terminus, preferably a water-soluble polymer having a maleimide structure, is used in binding reaction with the thiol group of cysteine. For binding PEG having a particularly desirable molecular weight of 10,000 to 60,000 to the cysteine residue in the amino acid sequence of interferon-β, it is preferred to use interferon-β having a sugar chain smaller than natural one, interferon-β from which a sugar chain has been removed, or interferon-β originally having no sugar chain. The use of such interferon-β allows binding reaction without reductive dissociation to proceed a thigh efficiency in a single step.

After binding reaction, unreacted interferon-β and PEG and by-products can be removed by any of or any combination of methods such as chromatography using an ion exchange carrier, a gel filtration carrier, or a hydrophobic or hydrophilic carrier, to purify or concentrate the desired interferon-β complex having PEG bound with lysine located at the 19th or 134th position.

One of methods to most efficiently purify and concentrate the interferon-β complex having PEG bound with lysine located at the 19th or 134th position is chromatogram using an ion exchange carrier. The ion exchange carrier used is preferably a cation exchange carrier, more preferably a carrier where a sulfopropyl, sulfonic acid, or carboxymethyl group is attached to a base material, and any of these ion exchange carriers is commercially available. For example, when HiTrap SP HP (Amersham Pharmacia), Poros HS (Applied Biosystems), or SP-5PW (Tosoh) is used, a di-PEGylated interferon-β complex present in trace amounts in the reaction solution is initially eluted by a salt-concentration gradient. Subsequently, the desired interferon-β complex having PEG bound with lysine located at the 19th position in the amino acid sequence of interferon-β is eluted at a proportion of 40% or more of the total eluted fractions, followed by the elution and fractionation of complexes having PEG bound with N-terminal amino group or lysine located at the 33rd, 46th, or 108th position as minor isomers of PEG-bound sites, and unreacted interferon-β. In this procedure, the interferon-β complex having PEG bound with lysine located at the 134th position can be isolated at the same time.

Binding to the cation exchange carrier is performed by adjusting the reaction solution to ion strength suitable for the binding at pH 3.0 to 8.0. In this case, the cation exchange carrier may be loaded onto a column or suspended in the reaction solution. However, when the aggregation of an unreacted hydrophilic polymer in the cation exchange carrier reduces the separation efficiency of the desired complex, it is preferred to load the carrier onto the column after suspending and binding to perform elution. Elution from the cation exchange carrier can be performed by conducting stepwise gradient or isocratic elution with increasing salt concentrations or pH in a buffer solution composed of citrate, acetate, phosphate, or the like.

The PEG-bound site in the fractionated and eluted interferon-β complex can be analyzed, as described in Example 3, by peptide mapping, followed by the amino acid analysis or sequencing of the obtained PEG-bound fragment.

The antiviral activity of the interferon-β complex having PEG bound with lysine located at the 19th or 134th position thus produced can be measured with ease by a method known in the art (e.g., Armstrong, J. A., Methods In Enzymology, 78, 381-387, (1981); Rubinstein et al., J. Virol. 37, 755 (1981); and Borden et. al., Canc. Res. 42, 4948 (1982)). Interferon-β having 40,000-molecular weight PEG bound with lysine located at the 19th position maintains 10% or higher of activity before binding, and this activity is equivalent to the activity of interferon-β bound with PEG having a molecular weight of 20,000. Alternatively, interferon-β having 40,000-molecular weight PEG bound with lysine located at the 134th position maintains 70 to 100% of activity before binding. The remaining activity of a complex having 40,000-molecular weight PEG bound with the N terminus of interferon-β has previously been reported to be 0% (Pepinsky et al., The Journal of Pharmacology and Experimental Therapeutics, vol. 297, p 1059-1066, (2001)). Accordingly, this demonstrates that the use of the lysine located at the 19th or 134th position as the high molecular weight PEG-bound site of interferon-β is exceedingly useful.

The method of the present invention can also be applied to substances other than PEG as a method for producing a complex without reduction in interferon-β activity. Preferably, the substance other than PEG has an amino-reactive structure such as a hydroxysuccinimide ester or nitrobenzene sulfonate ester structure. This second molecule is not limited to molecules for conferring in vivo stability such as PEG and serum proteins and may be a physiologically active substance having totally different function such as enzymes, cytokine, antibody molecules, or fragments thereof. A complex derived from any of these substances is useful for constructing a fusion molecule or labeling agent also having interferon-β activity.

In addition, the method of the present invention can be applied to the immobilization of interferon-β onto a variety of supports, for example, the flat surface or granule of a sugar, glass, or resin material. Namely, the use of the lysine located at the 19th or 134th position as a binding point between interferon-β and any of a variety of supports allows the immobilization of the interferon-β without reduction in its activity. This immobilization procedure requires introducing a cross-linking agent having a similar amino-reactive functional group or binding the cross-linking agent to the support in advance.

The complex between interferon-β and PEG of the present invention can be used in the treatment of a variety of diseases that exploits IFN biological activity. For example, the complex can be used in the treatment of chronic active hepatitis B, chronic hepatitis C, and other viral diseases; a variety of malignant neoplasms such as glioblastoma, medulloblastoma, astrocytoma, and malignant melanoma of skin; and autoimmune diseases such as multiple sclerosis. Furthermore, it can be used in the treatment of disease accompanying vascularization, for example, inflammatory disease (e.g., rheumatic arthritis or psoriasis), eye diseases (e.g., diabetic retinopathy, retinopathy of prematurity, neovascular glaucoma, Stevens-Johnson syndrome and its related disease, ocular pemphigoid and its related disease, chemical burn of cornea, or trachoma), and cancer (e.g., breast cancer, prostatic cancer, malignant melanoma, renal cancer, brain tumors, or Kaposi's sarcoma).

The interferon-β complex of the present invention can be administered through an oral or parenteral route, either directly or as a pharmaceutical composition prepared by mixing the complex with a pharmacologically acceptable carrier or excipient known in the art. However, administration performed by hypodermic, intramuscular, or intravenous injection is preferred.

Concrete examples of a dosage form for oral administration include tablets, pills, capsules, granules, syrups, emulsions, and suspensions. Such dosage forms are produced by a method per se known in the art and contain a carrier or excipient typically used in a pharmaceutical field.

Examples of the carrier or excipient for tablets include lactose, maltose, saccharose, starch, and magnesium stearate. Examples of a dosage form for parenteral administration include eye-drops, ointments, injections, poultices, suppositories, transnasal absorption agents, transpulmonary absorption agents, transdermal absorption agents, and locally sustained-release agents.

Liquid preparations can be prepared by a method known in the art, for example, by dissolving or suspending the interferon-β complex in a sterile aqueous solution typically used for injections or by the emulsification or the embedding into liposome, of the interferon-β complex.

Solid preparations can be prepared by a method known in the art, for example, by adding an excipient such as mannitol, trehalose, sorbitol, lactose, or glucose to the interferon-β complex to make a freeze-dried product. This freeze-dried product can further be powdered, or otherwise, this powder can be mixed and solidified with polylactic acid or glycolic acid for use.

Gelling agents can be prepared by a method known in the art, for example, by dissolving the interferon-β complex in a thickener or polysaccharide such as glycerin, polyethylene glycol, methylcellulose, carboxymethylcellulose, hyaluronic acid, or chondroitin sulfate. Any of these preparations can be supplemented with human serum albumin, human immunoglobulin, α2-macroglobulin, amino acid, or the like, as a stabilizer and can be supplemented with alcohol, sugar alcohol, an ionic surfactant, a nonionic surfactant, or the like, as a dispersant or absorption promoter within a range that does not impair IFN biological activity. Alternatively, trace metal or a salt of an organic acid can optionally be added thereto.

The dose of the complex of the present invention is appropriately determined according to the age and body weight of a patient, disease or symptoms to be treated, an administration form and route, the molecular weight of PEG, and so on. However, in general, the complex of the present invention is administered within a range of one dose/month to one dose/day, preferably one dose/month to one dose/week, with 1,000 units to 100 million units/dose, preferably 10,000 units to 18 million units/dose.

EXAMPLES

Hereinafter, the present invention will be described more fully with reference to Examples.

Example 1

Effect of Additive on Binding Reaction of Polyethylene Glycol Activated with Hydroxysuccinimide Ester to Amino Group in Recombinant Interferon-β:

Glucose, glycerol, or ethylene glycol was added at each final concentration of 1, 5, 10, and 20% to recombinant human interferon-β (final concentration: 200 μg/ml; which was expressed and purified with recombinant *Escherichia coli* according to the method of Goeddel et al, Nucleic Acid. Res. Vol. 8, 4057-4074 (1980)) stored in 0.5 M sodium chloride and 100 mM acetate buffer solution (pH 5.0). The pH of these solutions and a control free of the additive was adjusted to 7.8 using 1 M disodium hydrogenphosphate solution. Polyethylene glycol (average molecular weight: 40K; manufactured by Shearwater Polymers, INC and purchased from NOF Corp) activated with hydroxysuccinimide ester was mixed at a molar ratio of approximately 10 per mole of interferon-β with each of the resulting solutions, followed by binding reaction overnight at 4° C. After reaction, unreacted interferon-β was removed, and interferon-β activity in each of the prepared reaction solutions was measured.

The measurement of the activity was performed using enzyme antibody technique (sandwich immunoassay) (see Eiji Ishikawa, "Enzyme Immunoassay" 3rd Ed., p. 180, Igaku-shoin). Specifically, rabbit anti-interferon-β antibodies were immobilized on an immunoplate, to which enzyme-labeled mouse monoclonal antibodies that recognized only active interferon-β structures were then added together with the sample. After the washout of unbound products, a color substrate was added to the immunoplate to calculate the interferon-β activity of the sample by comparison with the coloring value of a standard (a result on interferon-β activity was confirmed to be equal to a result obtained by a biological activity measurement method based on the antiviral activity of cultured cells). Meanwhile, the addition of a surfactant Tween 80 or HCO-60 in the same way as above suppressed the aggregation of interferon-β and however, also largely suppressed the progression of the binding reaction of PEG, leading to unsuccessful measurement of the activity of the conjugate.

As shown in Table 1, an evident effect of improving activity was observed in the reaction solution containing a proper amount of glucose, glycerol, or ethylene glycol, as compared with the control (activity of the PEG-interferon-β complex obtained by the binding reaction of PEG in the absence of the additive).

TABLE 1

| | | Interferon-β activity (10E+7 IU) | |
|---|---|---|---|
| Additive | Concentration(%) | Per reaction solution | Per weight of protein |
| 1 Glucose | 1 | 1.79 | 1.62 |
| 2 | 5 | 1.95 | 2.46 |
| 3 | 10 | 2.49 | 4.96 |
| 4 | 20 | 2.62 | 5.03 |
| 5 Glycerol | 1 | 2.28 | 1.73 |
| 6 | 5 | 2.19 | 1.87 |
| 7 | 10 | 2.53 | 1.81 |
| 8 | 20 | 2.51 | 2.24 |
| 9 Ethylene glycol | 1 | 1.74 | 1.37 |
| 10 | 5 | 2.24 | 1.68 |
| 11 | 10 | 2.77 | 2.04 |
| 12 | 20 | 2.96 | 2.37 |
| 13 Absent | | 1.70 | 1.09 |

Example 2

Separation and purification of interferon-β complex having polyethylene glycol bound with amino group of lysine located at 19th position:

Ethylene glycol was added at the final concentration of 20% to recombinant human interferon-β (final concentration: 200 μg/ml) stored in 0.5 M sodium chloride and 100 mM acetate buffer solution (pH 5.0), followed by pH adjustment to 7.6 using 1M disodium hydrogenphosphate solution. Polyethylene glycol (average molecular weight: 40K; purchased from NOF Corp) activated with hydroxysuccinimide ester was mixed with the resulting solution, followed by binding reaction overnight at 4° C. The reaction solution was dialyzed overnight at 4° C. against 20 mM acetate buffer solution (pH 4.5) containing 10 mM NaCl-0.05% Tween 20. The dialyzed solution was applied to a cation exchange column Poros HS 1.7 mL-gel (manufactured by Applied Biosystems) or SP-5PW (Tosoh). Elution was performed by increasing the proportion of Solvent B (20 mM acetate buffer solution (pH 4.5 to 4.7) containing 1 M NaCl) mixed to Solvent A (20 mM acetate buffer solution (pH 4.5 to 4.7) containing 10 mM NaCl). Specifically, elution was performed by stepwise increasing the proportion of Solvent B to 30, 40, 50, and 100% in the Poros HS column and by using 0 to 100% continuous gradient in the SP-5PW column. An absorbance chromatogram obtained by elution with the Poros HS column is shown in FIG. 1. Components on the absorbance chromatogram eluted by increasing stepwise the proportion of Solvent B to 30, 40, 50, and 100% are designated as peaks 1 to 4 (in the drawing, (i) to (iv)), respectively.

Figure 2:
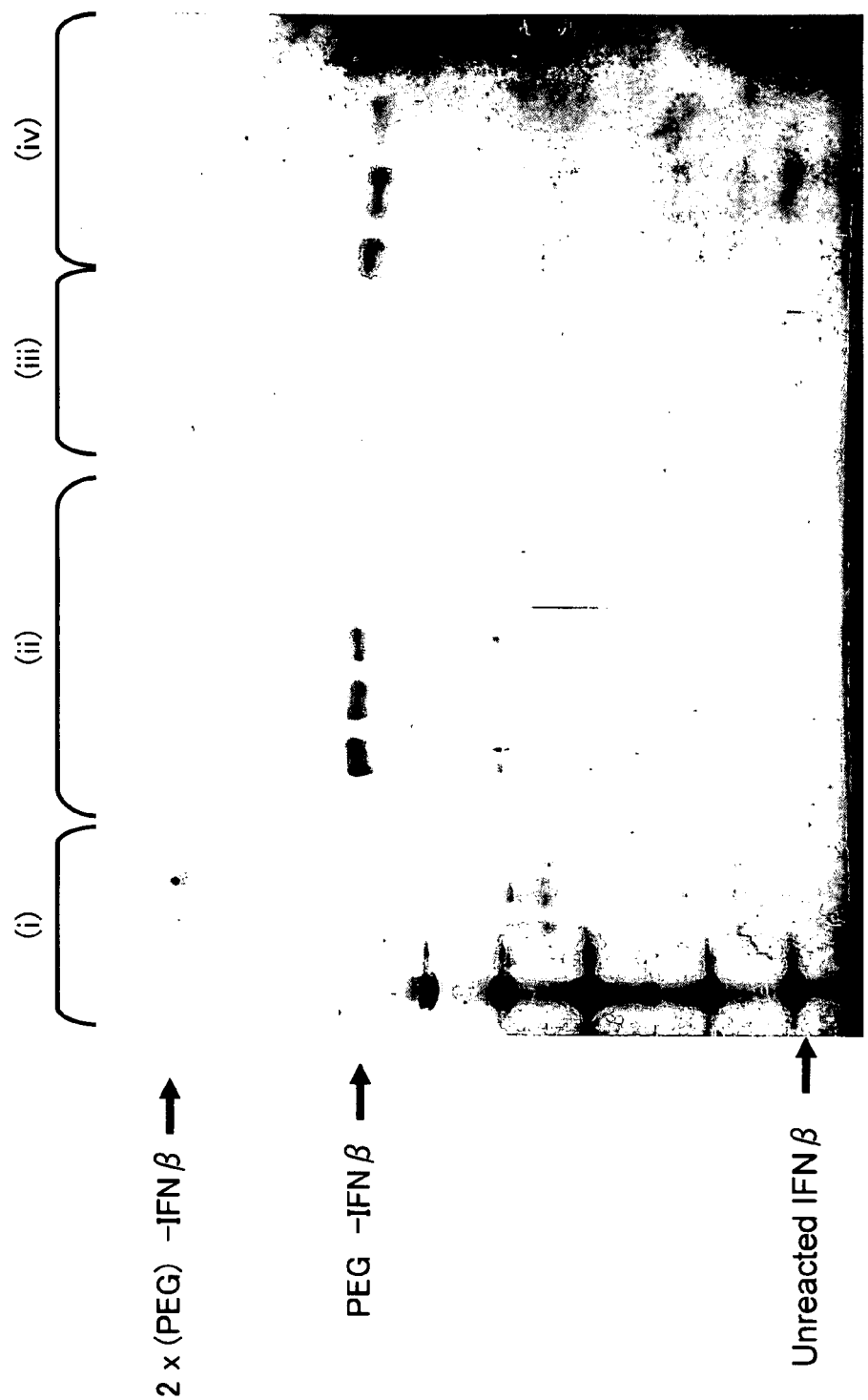
FIG. 2 is a diagram showing a result of analyzing components of peaks 1 to 4 (in the drawing, (i) to (iv)) obtained by the Poros HS column separation and purification of an interferon-β complex having polyethylene glycol bound with the amino group of lysine located at the 19th position, wherein the components are separated by SDS-PAGE and then analyzed by silverstaining.

A result of analyzing each peak component (1 to 4) by silver staining after SDS-PAGE separation is shown in FIG. 2. The desired interferon-β complex having 40K-molecular weight PEG bound with the lysine residue located at the 19th position could be obtained in the peak 2. Minor isomers of PEG-bound sites that could not quite be controlled by reaction could be separated as by-products, which include an interferon-β complex having PEG bound with a lysine residue located at the 33rd position (in the peak 3) and an interferon-β complex having PEG bound with an N-terminal amino group or a lysine residue located at the 108th or 134th position (in the peak 4). Unreacted interferon-β and di-PEGylated interferon-β could be separated in the peaks 4 and 1, respectively.

Figure 3:
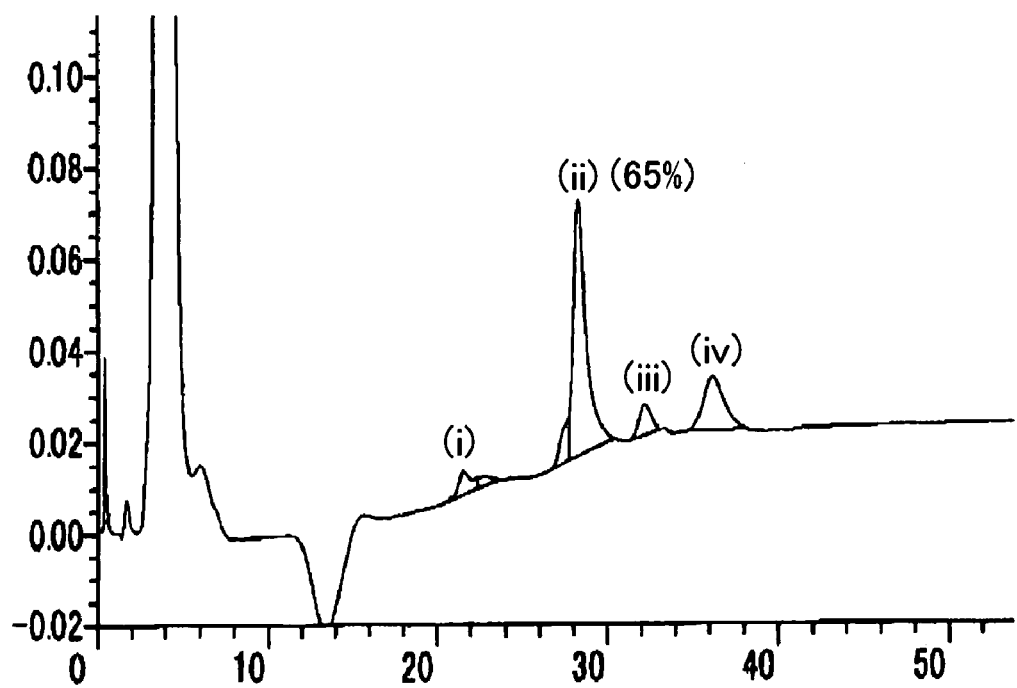
FIG. 3 is a diagram showing the SP-5PW column separation and purification of an interferon-β complex having polyethylene glycol bound with the amino group of lysine located at the 19th position.

An absorbance chromatogram obtained by elution with the SP-5PW column is shown in FIG. 3. The SP-5PW column was capable of separation similar to the Poros HS column separation. The desired interferon-β complex having 40K-molecular weight PEG bound with the lysine residue located at the 19th position accounted for, as the peak 2, approximately 65% of the total amount of proteins (its proportion was 65% or more to all PEGylated complexes except unreacted interferon-β).

Example 3

Confirmation of polyethylene glycol-bound site of recombinant interferon-β:

Each peak fraction separated with the SP-5PW column in Example 2 was desalted and concentrated with a solid-phase extraction cartridge (OASIS HLB; Waters) and then exsiccated with a centrifuge evaporator. The resulting product was dissolved in a Tris buffer solution (pH 9) containing 6 mol/L guanidine, followed by Cys reduction with dithiothreitol and carboxyamidomethylation with iodoacetamide. After the addition of lysyl endopeptidase, the resulting mixture was incubated at 37° C. for 5 hours to perform structure-specific digestion. The enzyme reaction was terminated with acetic acid to make a pretreated sample for analysis.

This sample was subjected to reverse-phase HPLC analysis under the following conditions: column: Cadenza CD-C (184.6×150); detection wavelength: 214 nm (UV); column temperature: 40° C.; flow rate: 0.8 mL/min; mobile phase A: acetic acid/TFA/distilled water (1/0.2/1000); mobile phase B: acetic acid/TFA/acetonitrile/distilled water (0.9/0.2/800/200); gradient: 5% to 70% mobile phase B in 80 min, followed by 70% to 100% mobile phase B in 5 min; and analysis cycle: 120 min.

Figure 5:
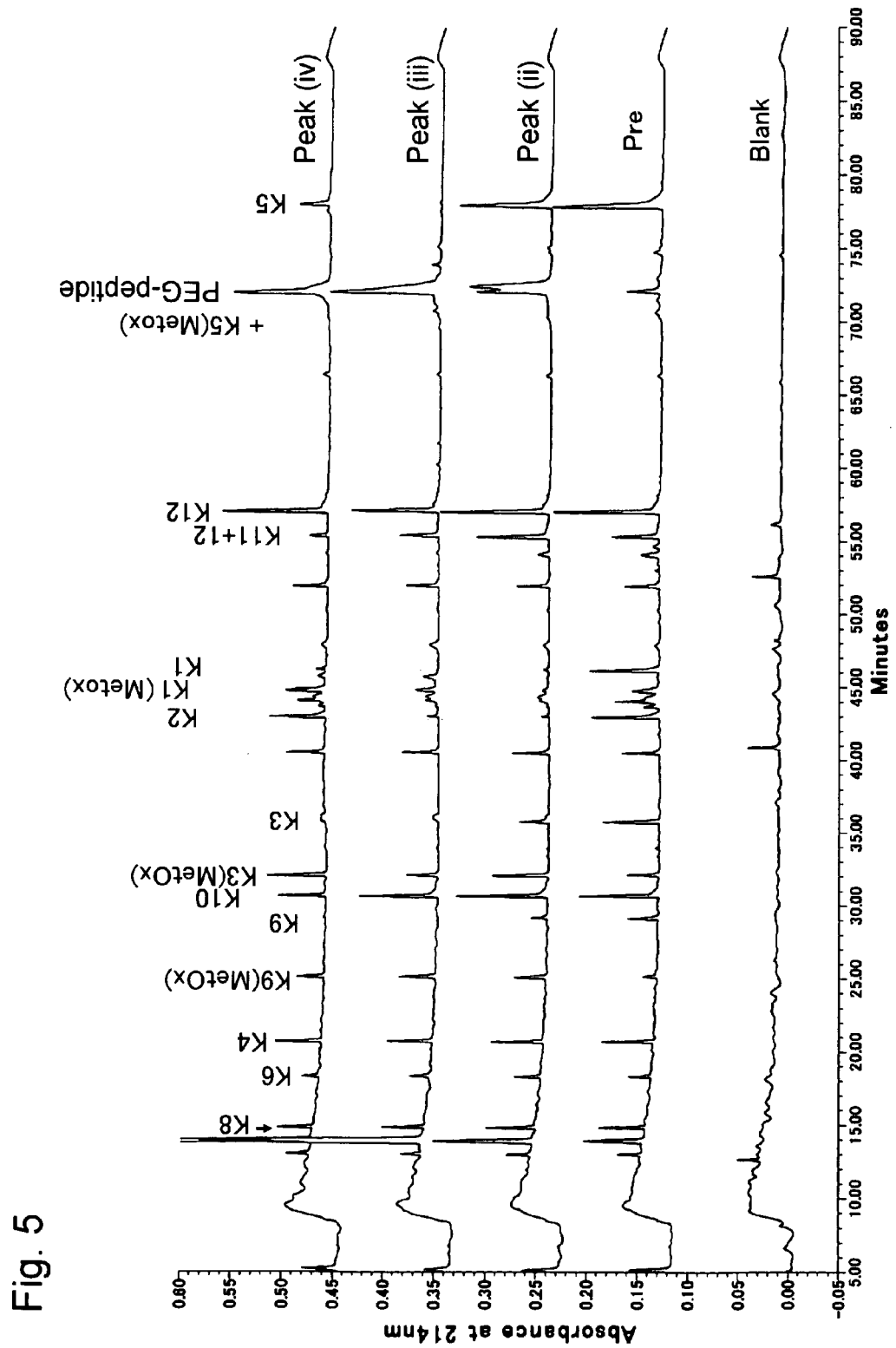
FIG. 5 is a diagram showing the peptide map (treated with lysyl endopeptidase) of eluted components of peaks 2 to 4 (in the drawing, indicated by (ii) to (iv)) separated with SP-5PW column after binding reaction with PEG having a molecular weight of 40K as well as the peptide map of interferon-β(in the drawing, indicated by Pre in the lowermost part) before reaction with PEG.

Peaks (K1 to K12) in HPLC chromatogram corresponding to lysyl endopeptidase digestion fragments of interferon-β before the binding reaction of PEG are shown in FIGS. 4 and 5-pre. The arrows in FIG. 4 denote lysyl endopeptidase cleavage sites. Peptide fragments generated by cleavage were designated as K1 to K12. The symbols K1 to K12 in FIG. 5 correspond to the peptide fragments K1 to K12 in FIG. 4, respectively. In contrast, the remarkable decrease of the peptide fragments K1 and K2 was observed in the peptide map of the peak 2, as shown in FIG. 5-2 (in the drawing, (ii); hereinafter, specified in the same way). This is probably because the introduction of PEG to the amino group on the side chain of lysine located at the 19th position allowed this site to circumvent lysyl endopeptidase digestion, resulting in no generation of the peptide fragments K1 and K2. From this result, the site where PEG was introduced was estimated to be lysine located at the 19th position.

The peptide map of the peak 3 produced a result shown in FIG. 5-3, in which the remarkable absent of the peptide fragment K2 was observed. This is probably because the introduction of PEG to the amino group on the side chain of lysine located at the 33rd position allowed this site to circumvent lysyl endopeptidase digestion, resulting in no generation of the peptide fragment K2. From this result, the main site where PEG was introduced was estimated to be Lys 33.

Because a decrease in the peptide fragment K1 was observed in the peak 4 as shown in FIG. 5-4, the presence of an N-terminal conjugate was estimated. In addition, the peptide fragment K10 was decreased one-half, suggesting that a Lys 134 or Lys 123 isomer was likely to be contained.

Next, a PEG-peptide conjugate fragment that appeared as a peak around 75 minutes in the reverse-phase HPLC analysis of peaks was subjected to amino acid sequence analysis. This result and information obtained from the peptide map demonstrated that the peak 2, a main reaction product, is the desired complex having PEG bound with lysine located at the 19th position. A positional isomer having PEG bound with lysine located at the 33rd position and a positional isomer having PEG bound with lysine located at the 134th or 108th position or the N terminus were separated in the peaks 3 and 4, respectively, as minor by-products.

Example 4

Measurement of remaining activity of interferon-β complex having 40K- or 20K-molecular weight peg selectively bound with lysine residue located at 19th position:

A recombinant human interferon-β complex having 40K- or 20K-molecular weight PEG selectively bound with the lysine residue located at the 19th position was synthesized, isolated, and purified by the method of Example 2, followed by activity comparison with recombinant human interferon-β before PEG binding. The comparison of interferon-β activity was made by measuring antiviral activity. Specifically, the assessment was made by bioassay using human amniocytes FL cells in combination with sindbis viruses or vesicular stomatitis viruses (VSV) (Armstrong, J. A., Methods In Enzymology, 78, 381-387, (1981)).

As a result, the activity of recombinant human interferon-β before PEG binding was $1.22 \times 10^8$ MIU/mg, whereas the conjugate having 40K PEG had antiviral activity of $5.5 \times 10^7$ MfU/mg and a remaining activity value as high as 45%. The remaining activity of the conjugate having 20K PEG measured in the same way was 38.7%.

Example 5

Figure 6:
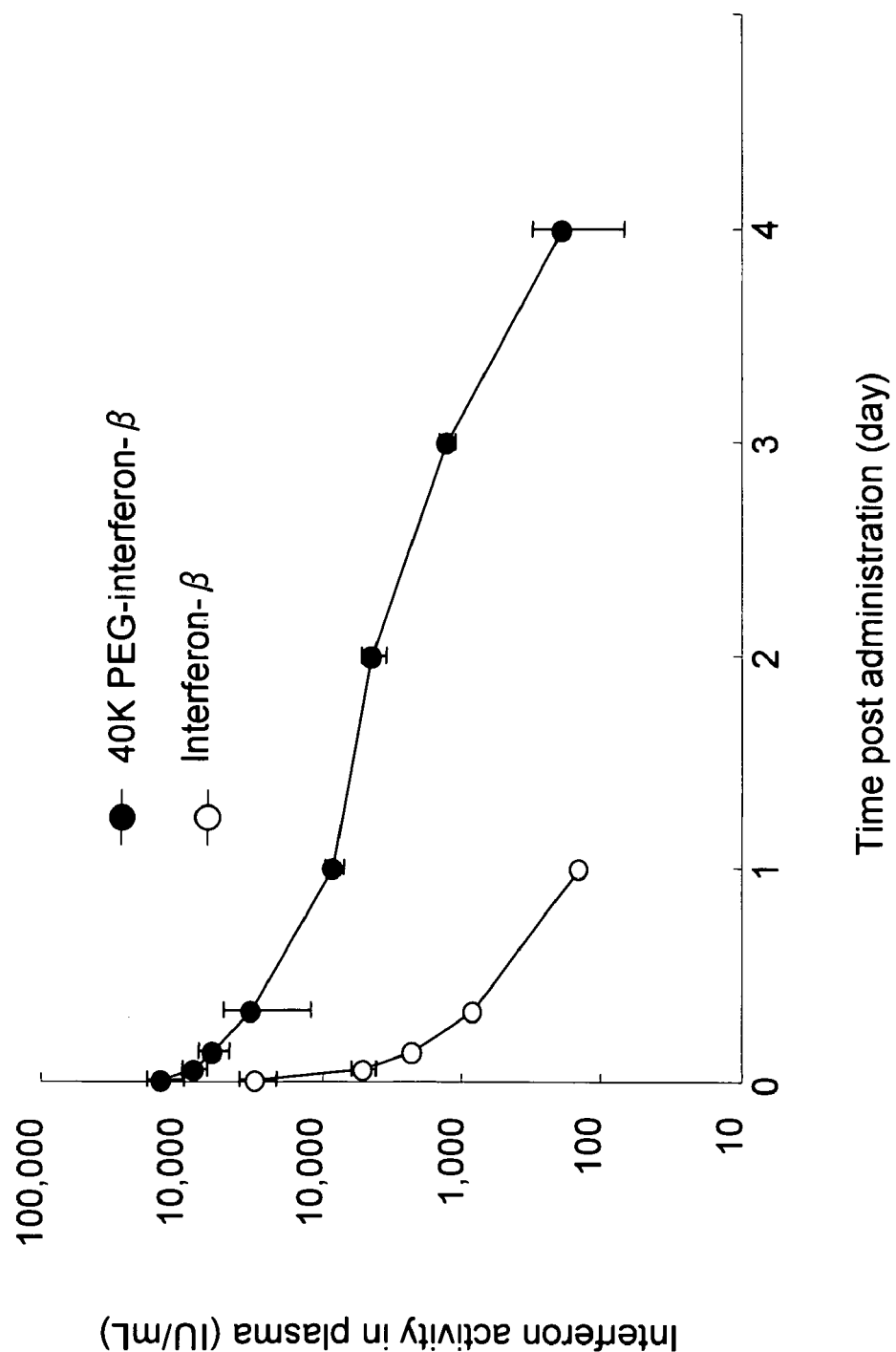
FIG. 6 is a diagram showing the retention, in rabbit blood, of interferon-β having 40K-molecular weight PEG bound with lysine located at the 19th position.
Figure 7:
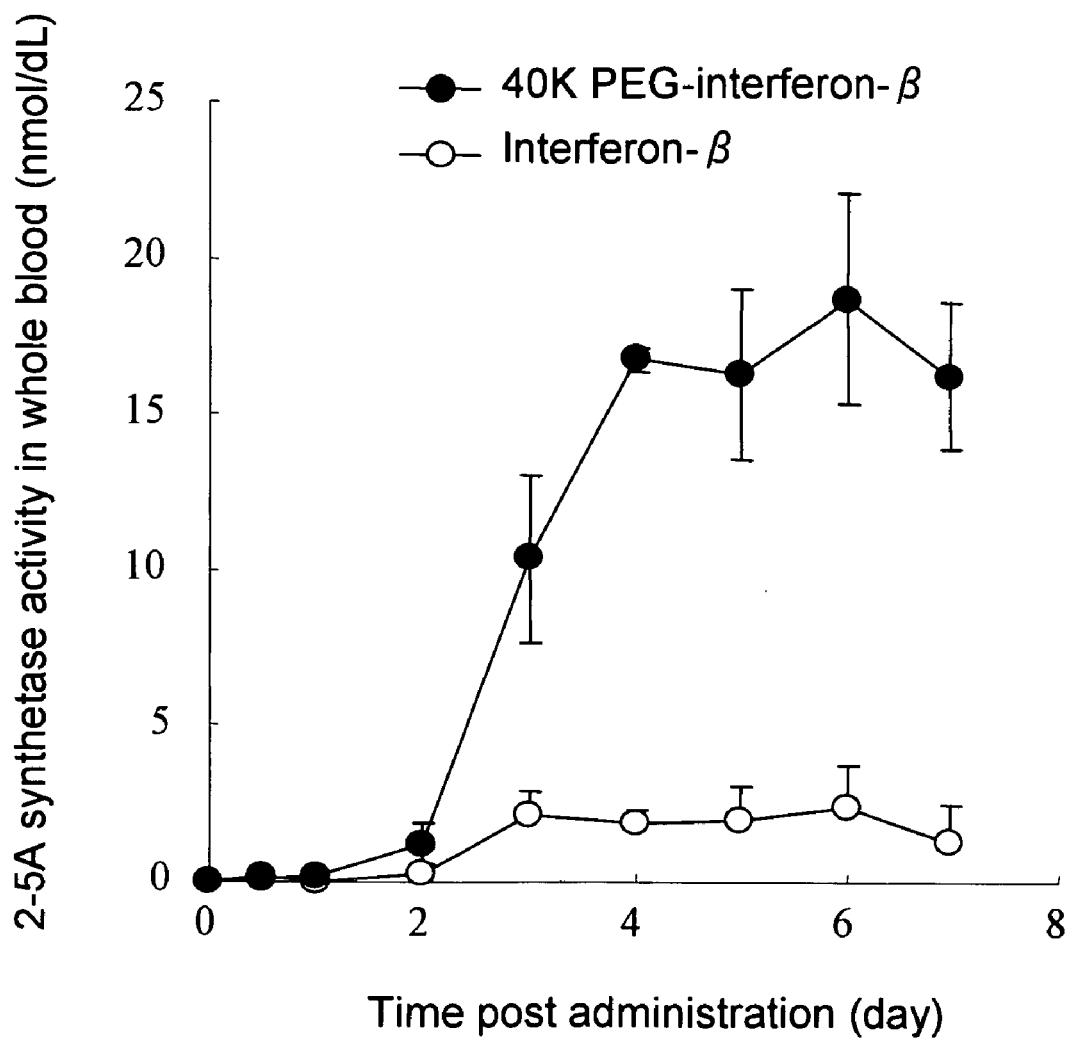
FIG. 7 is a diagram showing time course of induction of a pharmacological marker (2-5A synthetase activity) in a rabbit by interferon-β having 40K-molecular weight PEG bound to lysine located at the 19th position.

Pharmacokinetic analysis of interferon-β complex having 40K-molecular weight PEG selectively bound to lysine residue located at 19th position and evaluation of its activity of inducing pharmacodynamic marker:

A recombinant human interferon-β complex having 40K-molecular weight PEG selectively bound with the lysine residue located at the 19th position was synthesized, isolated, and purified by the method of Example 2. This interferon-β complex was administered at 9 MIU/kg to a rabbit (NZW, male). Blood was collected from the rabbit before administration and after 15 minutes, 1.5 hours, 3.5 hours, 8 hours, 1 day, 2 days, 3 days, 4 days, 5 days, 6 days, and 7 days of administration to measure antiviral activity in plasma and 2-5A synthetase activity in whole blood. The antiviral activity was measured by the method described in Example 1, while the 2-5AS synthetase activity was measured using 2-5A Kit "Eiken" (Eiken Chemical) according to the specified protocol. The time course of the remaining activity of interferon-β in blood based on the antiviral activity measurement is shown in graph form in FIG. 6. The time course of 2-5AS synthetase activity serving as a pharmacodynamic marker is shown in graph form in FIG. 7. The binding of PEG having a molecular weight of 40K resulted in 20.8-fold increase in the remaining activity (AUC) of interferon-β in blood. This increase led to a rise in the activity of inducing the pharmacodynamic marker (AUC was increased by 7.6 times by the binding of PEG and exceeded the highest value of the induction of the pharmacodynamic marker by unmodified interferon-β even after 7 days post administration).

Example 6

Separation and purification of interferon-β complex having polyethylene glycol bound with amino group of lysine located at 134th position:

A reaction solution of the binding between recombinant human interferon-β and PEG obtained in the same way as in Example 2 was supplemented with a 5-fold volume of 10 mM acetate buffer solution (pH 4.5) and applied to a cation exchange column (TOYOPEARL CM 650(S) (Tosoh)) equilibrated with the same buffer solution.

Figure 8:
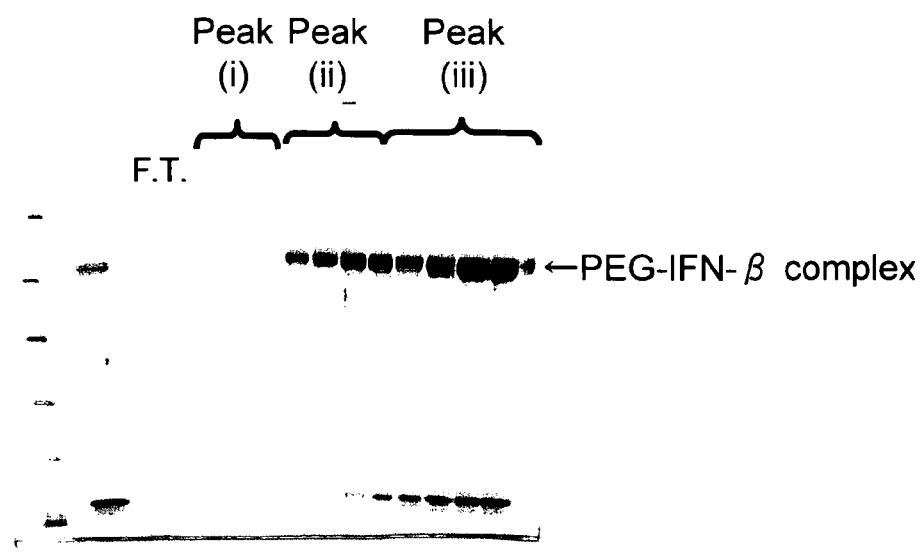
FIG. 8 is a diagram showing a result of analyzing peak fractions obtained by the TOYOPEARL CM 650 column separation of an interferon-β complex having polyethylene glycol bound with the amino group of lysine located at the 134th position, wherein the fractions are analyzed by SDS-PAGE (A), and the fraction of the peak 3 (in the drawing, (iii)) is further analyzed with SP-5PW column (B) (each of the chromatograph was lined from bottom to top in the order of elution)
Figure 8:
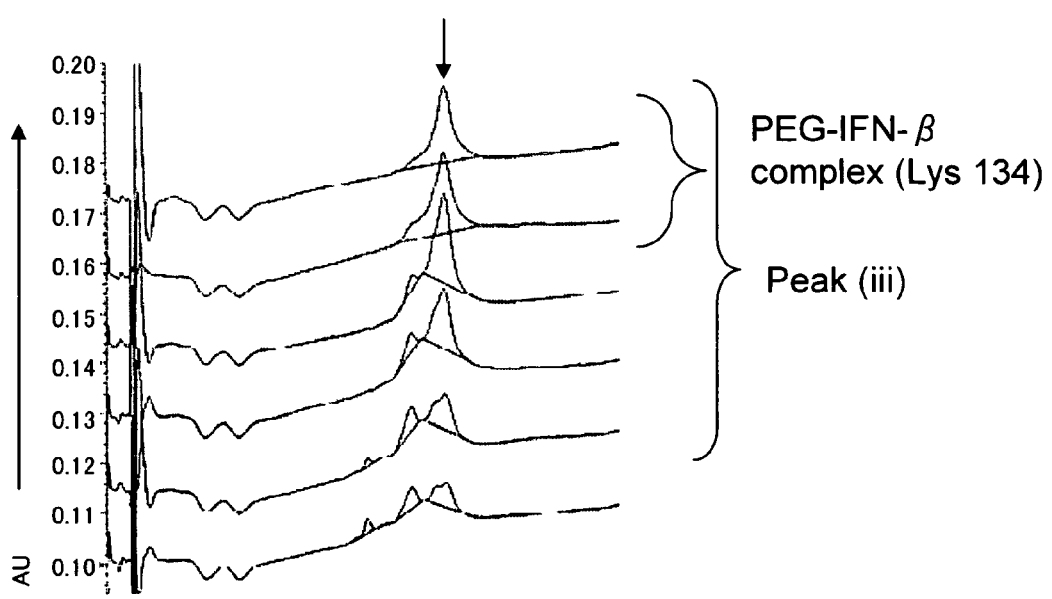

Proteins were eluted with the same buffer solution containing 1 M sodium chloride by increasing the proportion of the buffer solution mixed from 0 to 65% in a continuous gradient, and then fractionated. The eluted fractions were analyzed by SDS-PAGE and with SP-5PW column (Tosoh). The respective results are shown in FIGS. 8-A and 8-B.

As a result, three peaks were obtained as in Example 2. However, when the fraction contained in the third peak (peak (iii) in FIG. 8-A) was separately analyzed with the SP-5PW column, the fraction was shown to be further separated into several components (FIG. 8-B). Among these components, the fraction containing a peak (arrow in FIG. 8-B) that constituted the highest percentage of the third peak and was eluted last was analyzed in the same way as in Example 3. As a result, an IFN-β complex having PEG bound with lysine located at the 134th position was isolated therein.

Example 7

Comparison of activity between peg interferon-β complex obtained by nonselective binding reaction of peg to lysine and peg interferon-β complex obtained by selective binding reaction thereof:

Ethylene glycol was added at the final concentration of 20% to recombinant human interferon-β or natural interferon stored in 0.5 M sodium chloride and 100 mM acetate buffer solution (pH 5.0), followed by pH adjustment to 5.5 (reaction condition 1) or to approximately 7.6 (reaction condition 2) using 1M disodium hydrogenphosphate solution, in the same way as in Example 2. Polyethylene glycol (average molecular weight: 10K, 20K, or 40K; manufactured by Shearwater Polymers, INC and purchased from NOF Corp) activated with hydroxysuccinimide ester was mixed in a 45-fold amount relative to one interferon-β molecule with the resulting solution, followed by binding reaction overnight at 4° C.

At the same time, SDS was added at the final concentration of 0.1% to a recombinant human interferon-β or natural interferon-β solution, followed by the pH adjustment of the reaction solution to 9.0 (reaction condition 3). Polyethylene glycol (average molecular weight: 10K, 20K, or 40K) activated with hydroxysuccinimide ester was mixed in a 45-fold amount relative to one interferon-β molecule with the resulting solution, followed by binding reaction overnight at 4° C.

Interferon-β activity in each of the solutions after reaction was evaluated by the same antiviral activity measurement method as in Example 4. The progression of binding reaction in each of the solutions was confirmed by SDS-PAGE.

As shown in Table 2, interferon-β activity was decreased to 10% or less regardless of the molecular weight of PEG under the reaction condition 3 that did not secure the binding selectivity of PEG to lysine. On the other hand, at least 10% or higher of interferon-β activity was confirmed to be maintained regardless of the molecular weight of PEG under the reaction conditions 1 and 2 that enhanced the binding selectivity of PEG to lysine located at the 19th or 134th position.

TABLE 2

| | IFN-β type | | | | | |
|---|---|---|---|---|---|---|
| | Natural (sugar chain-linked) IFN-β | | | E. coli recombinant IFN-β | | |
| | PEG molecular weight | | | | | |
| | 40K | 20K | 10K | 40K | 20K | 10K |
| Reaction condition 1 | 100% | 86% | 94% | 94% | 54% | 61.9% |
| Reaction condition 2 | 54% | 29% | 15% | 48% | 21% | 22% |
| Reaction condition 3 | 1% | 2% | 1% | 2.8% | 0.7% | 1.5% |

Example 8

Figure 9:
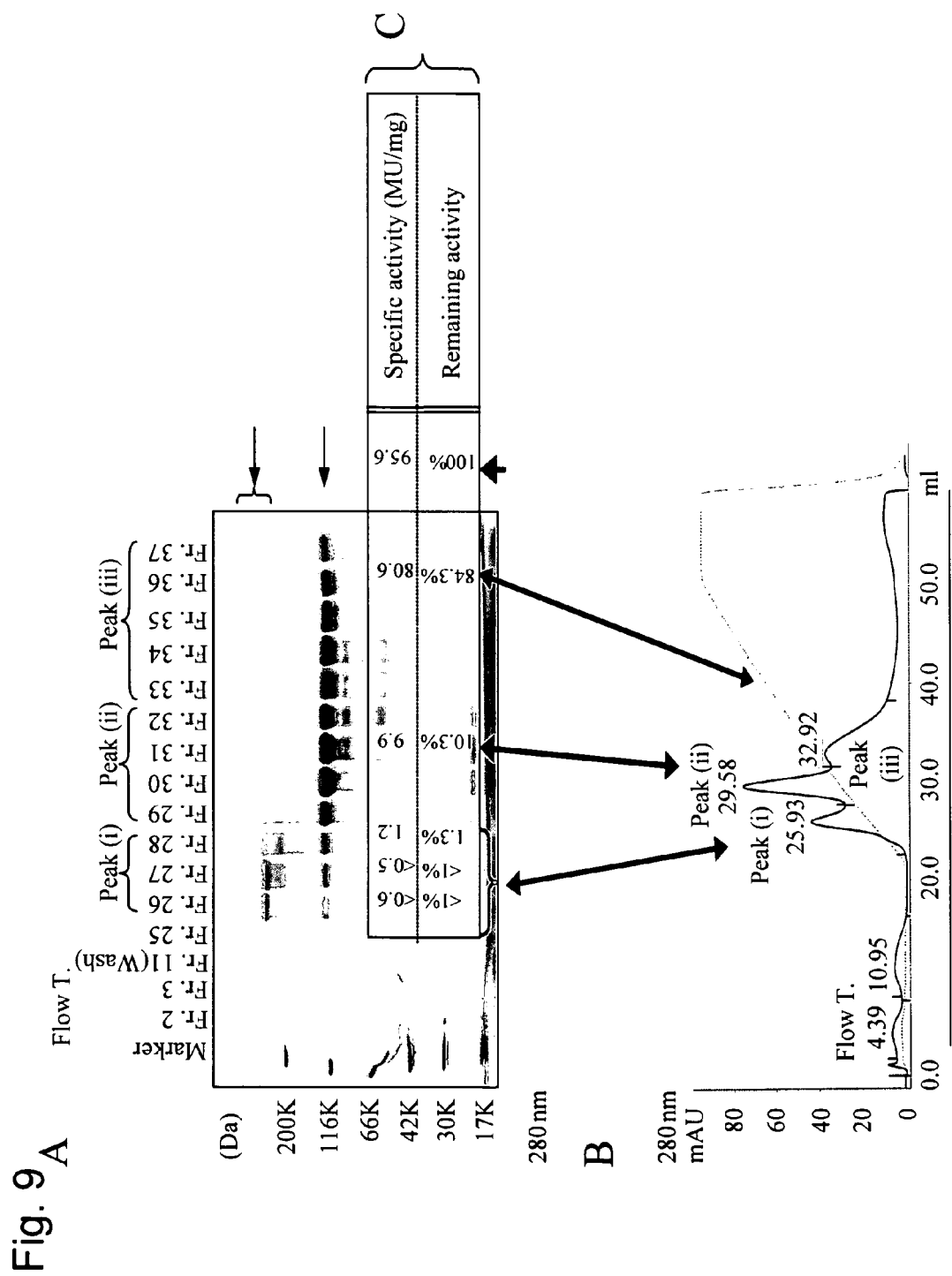
FIG. 9 is a showing the activities of a nonselectively multiply-PEGylated interferon-β complex with 2 or more PEG molecules and a mono-PEGylated interferon-β complex with PEG selectively bound with lysine located at the 19th or 134th position. In the drawing, a chromatogram obtained with TOYOPEARL CM 650(S) column (Tosoh) (B), a result of SDS-PAGE analysis corresponding to each separated fraction (A), and an antiviral activity value per amount of proteins of each fraction and an activity retention rate relative to the specific activity of IFN-β before PEG binding (C) are shown in correspondence with one another.

Comparison of activity between nonselectively multiply-PEGylated interferon-β complex with 2 or more PEG molecules and mono-PEGylated interferon-β complex with PEG selectively bound with lysine located at 19th or 134th position:

After the binding reaction of PEG in the same way as in Example 6, a fraction containing a nonselectively multiply-PEGylated interferon-β complex with 2 or more PEG molecules and a fraction containing a mono-PEGylated interferon-β complex with PEG selectively bound with lysine located at the 19th or 134th position were separated with TOYOPEARL CM 650(S) column (To soh) to measure their interferon-β activities by the method of measuring the antiviral activity described in Example 4. As a result, as shown in FIG. 9, the nonselectively multiply-PEGylated interferon-β complex with 2 or more PEG molecules maintained only approximately 1% activity, while the mono -PEGylated interferon-β complex with 40K PEG selectively bound with lysine located at the 19th or 134th position maintained 10% or more activity.

Example 9

Figure 10:
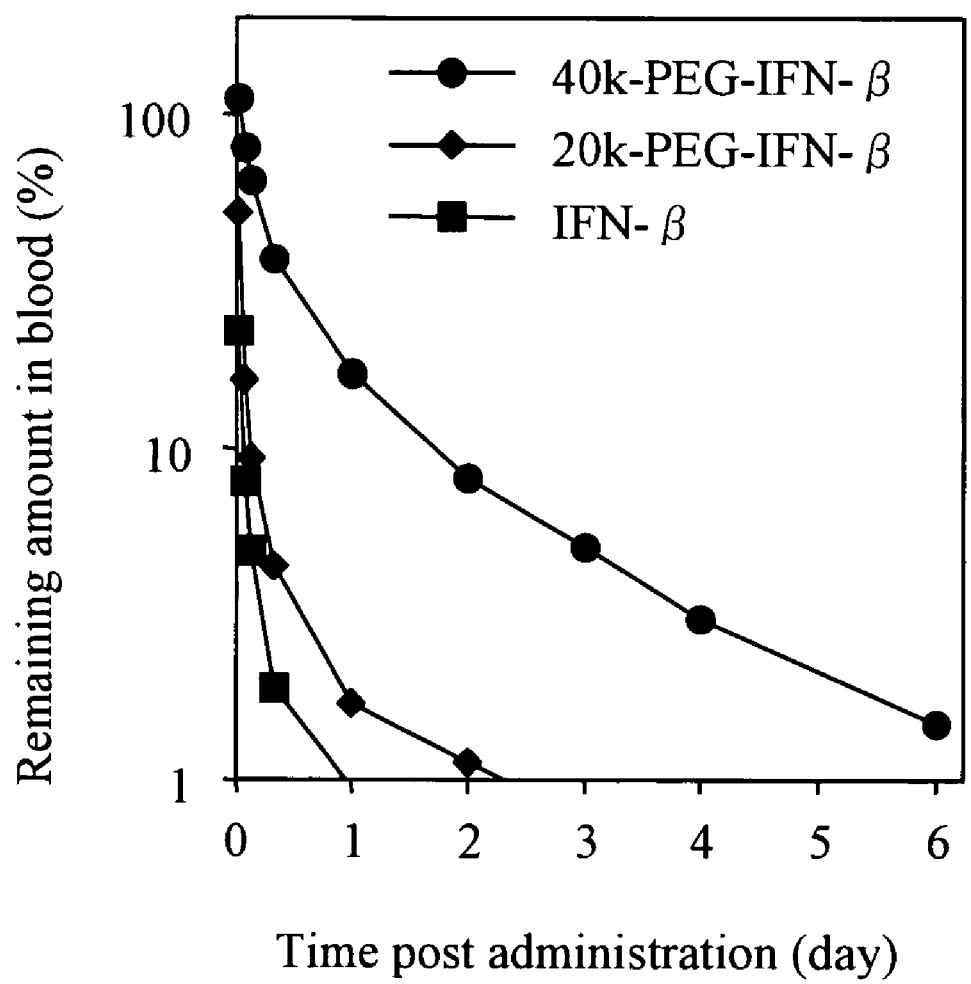
FIG. 10 is a diagram showing the retention, in blood, of an IFN-β complex bound with 20,000 (20K)- or 40,000 (40K)-molecular weight PEG, which has been administered intravenously into a rabbit.

Comparison of retention in blood between IFN-β complex bound with 20,000-molecular weight PEG and IFN-β complex bound with 40,000-molecular weight PEG:

IFN-β bound with 20,000- or 40,000-molecular weight PEG and non-PEGylated IFN-β were labeled with 125I and intravenously administered to a rabbit. Blood was chronologically collected from the rabbit up to 6 days. The amount of each interferon-β remaining in blood was measured by measuring radio activity with a γ-counter. Time course of the amount of interferon-β remaining in blood are shown in FIG. 10, with radio activity at the time of administration as 100%. The integral of the amount of interferon-β remaining in blood for IFN-β bound with 40,000-molecular weight PEG up to 6 days gave a rise 5.5 times greater than that of non-PEGylated IFN-β. The integral of the amount of interferon-β remaining in blood for IFN-β bound with 20,000-molecular weight PEG stayed at a rise 1.5 times greater than that of non-PEGylated IFN-β. This result demonstrated that it is important for the retention of the IFN-β complex in blood to bind 20,000 or more molecular weight PEG to IFN-β, with activity maintained.

All publications, patents, and patent applications cited herein are incorporated herein by reference in their entirety.

INDUSTRIAL APPLICABILITY

According to the present invention, polyethylene glycol can be bound specifically to lysine located at the 19th or 134th position in the amino acid sequence of interferon-β. An interferon-β complex produced by a method of the present invention maintains high activity, while having sufficient solubility and physical and biological stability as well as excellent circulatory half-life and clearance values, in living bodies. Thus, the interferon-β complex of the present invention produces fewer side effects and is useful as a highly effective pharmaceutical drug.

The invention claimed is:

1. An interferon-β complex produced by binding interferon-β comprising the amino acid sequence of SEQ ID NO: 1, or a mutant thereof which has antiviral activity and comprises a deletion of Met[1] and a substitution of Cys[17] with Ser in the amino acid sequence of SEQ ID NO: 1, wherein the interferon-β or the mutant thereof may or may not contain sugar chains, to polyethylene glycol, which has an average molecular weight of approximately 40,000 Da or above, at a lysine located at the 19$^{th}$ or 134$^{th}$ position of the interferon-β, or at a lysine located at a position corresponding thereto of the mutant, in an amino acid sequence of the interferon-β or the mutant thereof, in the presence of at least one additive selected from the group consisting of disaccharides, monosaccharides, sugar alcohols thereof, and $C_{2-3}$ polyhydric alcohols, wherein the antiviral activity of the complex is at least 10% of the antiviral activity of interferon-β before binding to polyethylene glycol.

2. A pharmaceutical composition comprising an interferon-β complex according to claim 1.

3. The interferon-β complex according to claim 1, wherein the interferon-β is natural or recombinant interferon.

4. The interferon-β complex according to claim 1, wherein the polyethylene glycol has an average molecular weight of approximately 40,000 Da to 60,000 Da.

5. The interferon-β complex according to claim 1, wherein the additive is selected from the group consisting of glucose, mannitol, sorbitol, sucrose, trehalose, ethylene glycol, and glycerol.

6. An interferon-β complex of interferon-β and polyethylene glycol, wherein the interferon-β is interferon-β comprising the amino acid sequence of SEQ ID NO: 1, or a mutant thereof which has antiviral activity and comprises a deletion of Met[1] and a substitution of Cys[17] with Ser in the amino acid sequence of SEQ ID NO: 1, wherein the interferon-β or the mutant thereof may or may not contain sugar chains, and wherein the polyethylene glycol, which has an average molecular weight of approximately 40,000 Da or above, is bound to a lysine located at the 19$^{th}$ or 134$^{th}$ position of the interferon-β, or a lysine located at a position corresponding thereto of the mutant, in the amino acid sequence of the interferon-β or the mutant thereof, wherein the antiviral activity of the complex is at least 10% of the antiviral activity of interferon-β before binding to polyethylene glycol.

7. The interferon-β complex according to claim 6, wherein the polyethylene glycol has an average molecular weight of approximately 40,000 Da to 60,000 Da.

8. A pharmaceutical composition comprising an interferon-β complex according to claim 6.

9. The interferon-β complex according to claim 6, wherein the interferon-β is natural or recombinant interferon.

* * * * *

UNITED STATES PATENT AND TRADEMARK OFFICE
CERTIFICATE OF CORRECTION

PATENT NO. : 7,691,975 B2
APPLICATION NO. : 10/569211
DATED : April 6, 2010
INVENTOR(S) : Narumi et al.

It is certified that error appears in the above-identified patent and that said Letters Patent is hereby corrected as shown below:

In Column 11
At line 65, please change "MfU/mg" to --MIU/mg--.

In Column 12
At line 20, please change "2-5A" to --2-5AS--.

Signed and Sealed this

Thirteenth Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,691,975 B2 Page 1 of 1
APPLICATION NO. : 10/569211
DATED : April 6, 2010
INVENTOR(S) : Narumi et al.

It is certified that error appears in the above-identified patent and that said Letters Patent is hereby corrected as shown below:

In Column 11
At line 67, please change "MfU/mg" to --MIU/mg--.

In Column 12
At line 20, please change "2-5A" to --2-5AS--.

This certificate supersedes the Certificate of Correction issued July 13, 2010.

Signed and Sealed this

Thirty-first Day of August, 2010

David J. Kappos
*Director of the United States Patent and Trademark Office*

SEQUENCE LISTING

<160> NUMBER OF SEQ ID NOS: 1

<210> SEQ ID NO 1
<211> LENGTH: 166
<212> TYPE: PRT
<213> ORGANISM: Homo sapiens

<400> SEQUENCE: 1

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```